United States Patent [19]

Martz

[11] Patent Number: 4,880,380

[45] Date of Patent: * Nov. 14, 1989

[54] ORTHODONTURE APPLIANCE WHICH MAY BE MANUALLY INSTALLED AND REMOVED BY THE PATIENT

[76] Inventor: Martin G. Martz, Park Central Office Building, Suite 301, 215 South Monarch St., Aspen, Colo. 81611

[*] Notice: The portion of the term of this patent subsequent to Dec. 27, 2005 has been disclaimed.

[21] Appl. No.: 108,427

[22] Filed: Oct. 13, 1987

[51] Int. Cl.⁴ .............................................. A61C 3/00
[52] U.S. Cl. ........................................ 433/11; 433/18; 433/22; 433/24
[58] Field of Search ..................... 433/11, 18, 8, 9, 10, 433/19, 20, 21, 22, 24

[56] References Cited

U.S. PATENT DOCUMENTS

| | | | |
|---|---|---|---|
| 1,292,702 | 1/1919 | Canning | 433/10 |
| 3,762,050 | 10/1973 | DalPont | 433/20 |
| 3,987,547 | 10/1976 | Moss | 433/11 |
| 4,273,530 | 6/1981 | Broussard | 433/6 |
| 4,505,672 | 3/1985 | Kurz | 433/6 |
| 4,604,057 | 8/1986 | Viglietti | 433/9 |

Primary Examiner—John J. Wilson
Attorney, Agent, or Firm—Flehr, Hohbach, Test, Albritton & Herbert

[57] ABSTRACT

There is disclosed herein an appliance for orthodonture characterized in that at least most of the appliance may be manually installed and removed by the patient, as required. This appliance includes a plurality of individual clasps for gripping onto individual upper or lower teeth of the patient. The clasps are configured such that they can be manually placed in gripping positions onto and manually disengaged from the teeth by the patient. At the same time, first and second continuous arch wires are connected at predetermined points along their lengths to the various clasps such that when the clasps are in gripping positions on their respective teeth, the wires extend from tooth to tooth along the facial and lingual sides of the teeth, respectively, and exert forces on the teeth to move the latter from malocclusion positions to desired, more ideal positions.

44 Claims, 5 Drawing Sheets

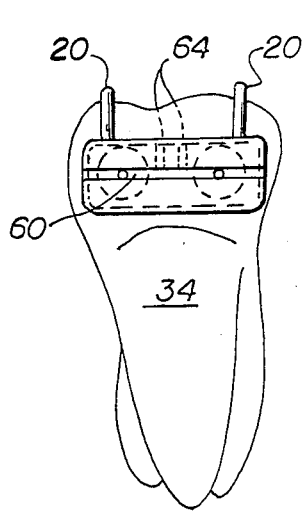
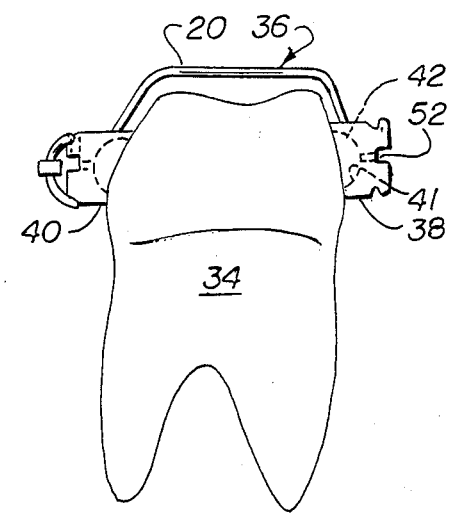
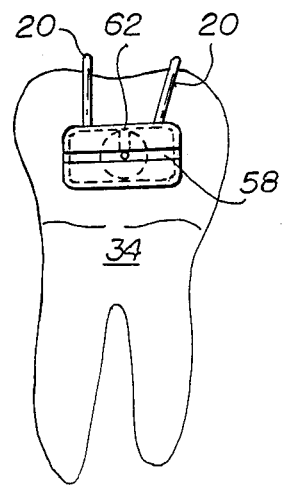
Fig.5C     Fig.5A     Fig.5B
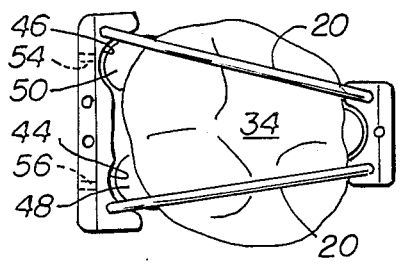
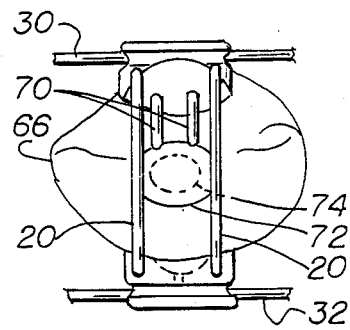
Fig.5D     Fig.6D
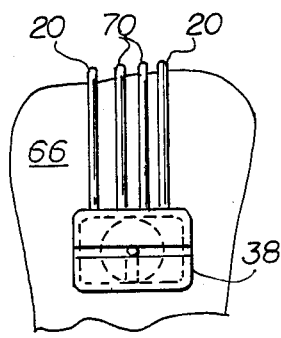
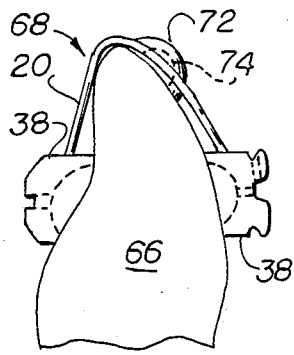
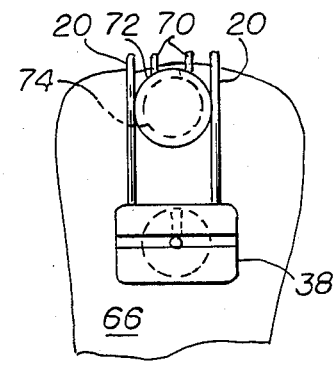
Fig.6C     Fig.6A     Fig.6B

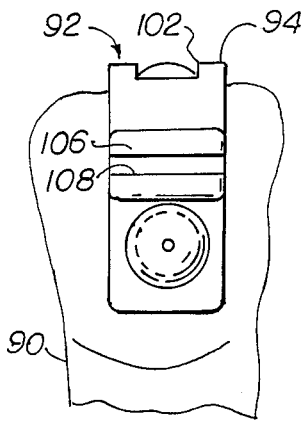
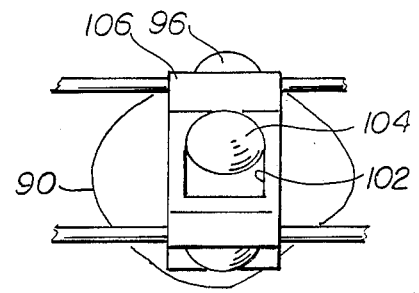
*Fig.8C*  *Fig.8D*
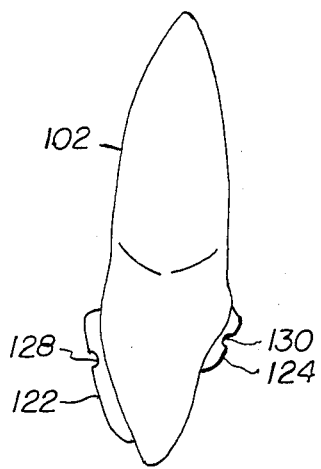
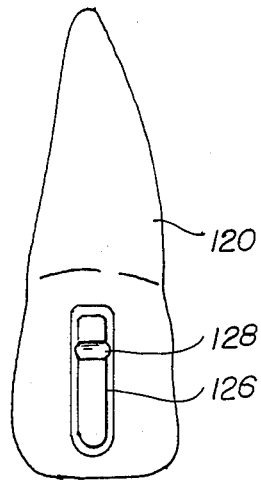
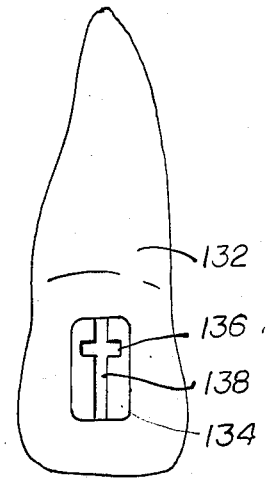
*Fig.9A*  *Fig.9B*  *Fig.10*
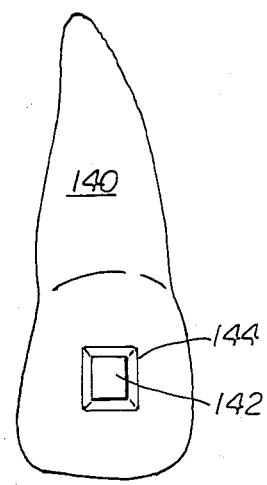
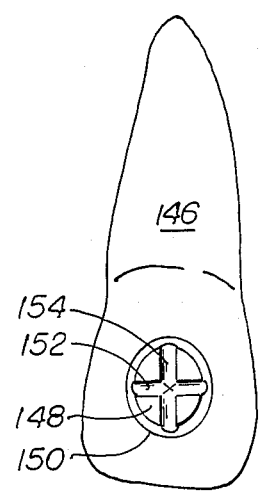
*Fig.11*  *Fig.12*

ORTHODONTURE APPLIANCE WHICH MAY BE MANUALLY INSTALLED AND REMOVED BY THE PATIENT

BACKGROUND OF THE INVENTION

1. Field of the Invention

This invention relates to a new and improved removable orthodontic appliance, namely, a tooth repositioning appliance and method. The present invention expands the range of treatments for a removable appliance by allowing the orthodontist to treat virtually all malocclusions, both major and minor. This new appliance can shift the position of the teeth within the upper or lower arch and also to move one dental arch relative to the other. Deep overbites or open bites may also be corrected. A feature of the invention is the fact that it is removable and the patient himself can remove and replace the appliances.

2. Description of Related Art

Removable orthodontic appliances are old in the art as are two-piece appliances. U.S. Pat. No. 4,505,672, for example, discloses upper and lower appliances for the upper and lower jaws and mechanical clasps and/or suction cups to attach the appliances to the teeth. Resilient means interconnect the two appliances. The present invention differs from the disclosure of the patent just recited in a number of respects, one being the provision of individual clasps, one for each tooth, connected together by a pair of continuous wires which biases the occluded teeth toward the desired position, as will be seen hereinafter.

In the main, other appliances heretofore used in the orthodontia profession have been permanent appliances which are adjusted from time to time by the orthodontist but otherwise remain fixed. One well-known example is the "Edgewise" appliance which consists of brackets fixed to the patient's teeth an fixedly supporting an arch wire which itself includes means for applying force to individual teeth. This appliance is intended to be permanent. As a result, the brackets cannot be continually installed and removed by the patient and the arch wire is fastened to the brackets. As will be seen hereinafter, a feature of the present invention is the fact that the device disclosed herein may be removed by the patient as required, particularly for eating, for cleaning the teeth and appliance, or for special occasions. It is anticipated that this appliance will be worn primarily at night although it could be worn full time.

SUMMARY OF THE INVENTION

The orthodonture appliance disclosed herein includes a plurality of individual clasps for gripping onto individual upper or lower teeth of the patient. These clasps are configured such that they can be manually placed in gripping positions onto and manually disengaged from the teeth by the patient. At the same time, at least one and preferably first and second continuous lengths of wire are connected by suitable means at predetermined points along their lengths to the various clasps such that when the clasps are in gripping positions on their respective teeth, the wire extend from tooth to tooth along the facial and/or lingual sides of the teeth, respectively, and exert forces on the teeth to move the latter from malocclusion positions to desired, more ideal positions.

Most of the various special techniques now in use for fixed appliances such as the use of loops or bends in the arch wires or the use of elastic bands or polymeric chains to open or close spaces can also be used with the appliance disclosed herein. It is possible that when some of these special techniques are utilized, the orthodontist may recommend that the appliances be left in place by the patient for a few days or weeks until a more stable appliance configuration is used, at which time it can then be removed by the patient whenever he desires to do so.

In a preferred embodiment of the present invention, each clasp consists essentially of two U-shaped spring tempered wire elements movable between biased contracted states and manually forced expanded states whereby to clamp to an associated tooth. These wires, extend over the occlusal surfaces of an associated tooth and in the preferred embodiment they extend over the mesial and distal marginal ridges. They are connected to the previously recited continuous wires by means of cooperating brackets fixedly connected to the ends of the U-shaped wires and disengagably connected with the continuous wires. In the same preferred embodiment, these connecting brackets include confronting recesses configured to receive cooperating projections (e.g., buttons) bonded onto the facial and lingual sides of associated tooth whereby to aid the clasp in clamping to its associated tooth.

IN THE DRAWINGS

FIGS. 5A-5D illustrate part of the orthodonture appliance designed in accordance with a second embodiment of the present invention;

Figure 4A:
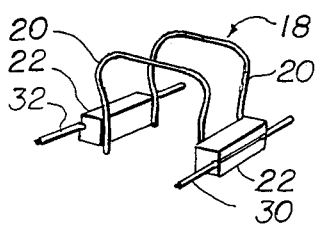
FIG. 4A is a perspective view of a part of the orthodonture appliance illustrated in FIGS. 1-3.
Figure 4B:
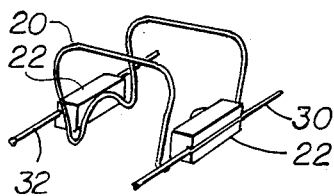
FIG. 4B is a perspective view of part of a modified appliance.
Figure 7A:
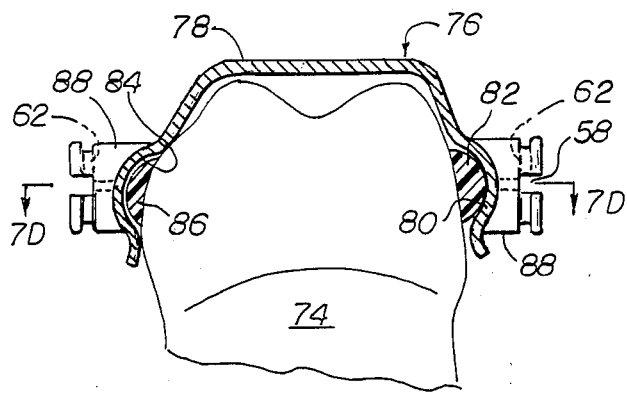
Figure 7B:
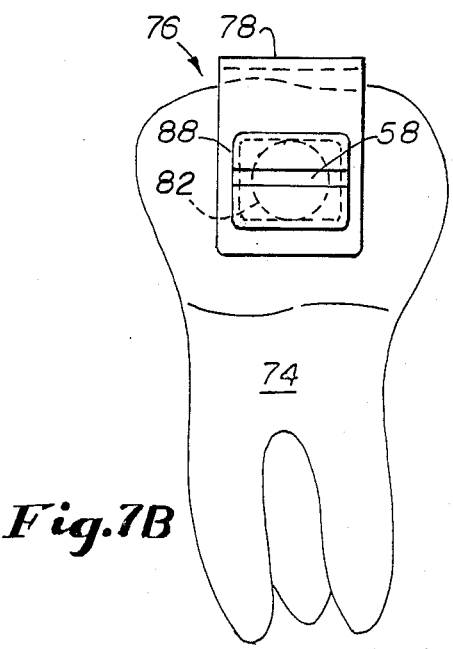
Figure 7C:
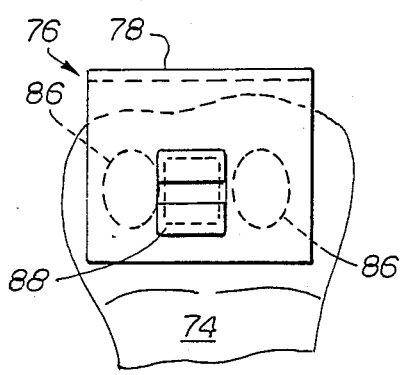
Figure 7D:
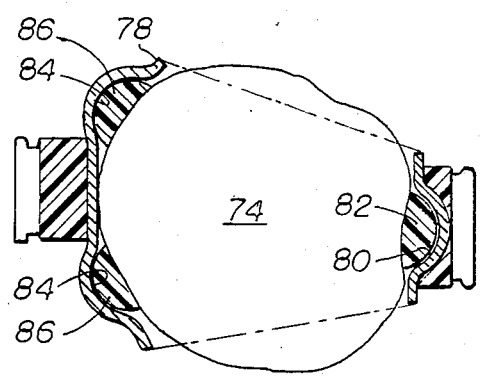
Figure 8A:
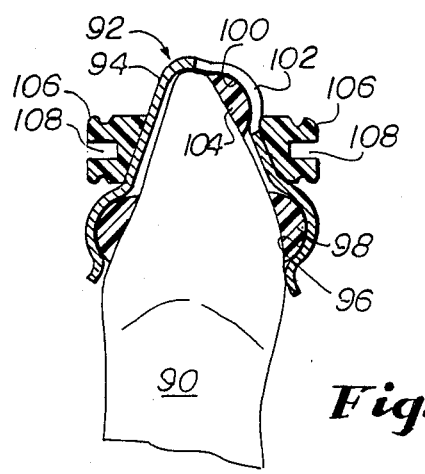
Figure 8B:
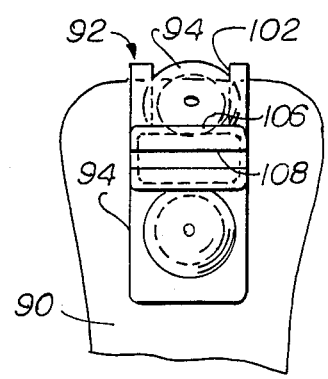
Figure 13:
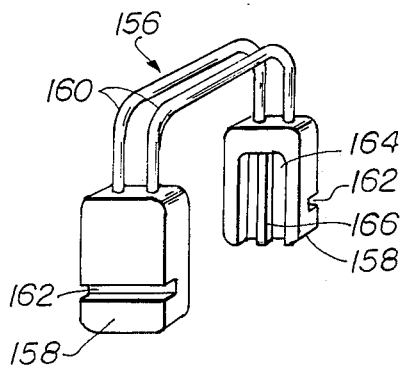
Figure 14:
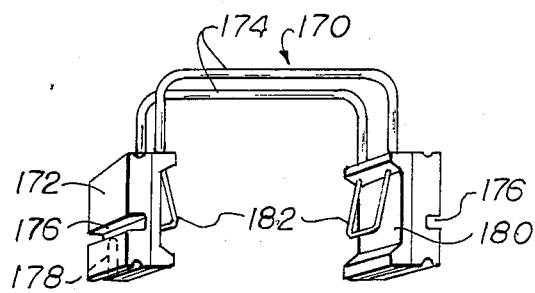
Figure 15:
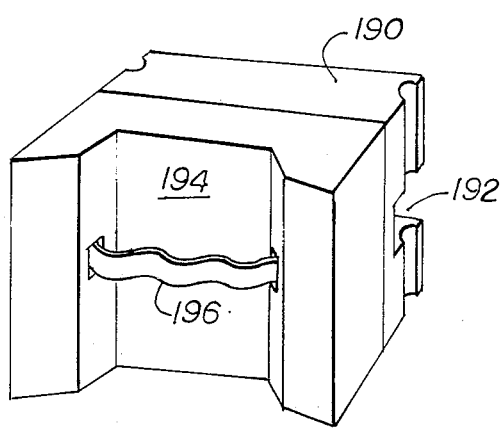
Figure 16:
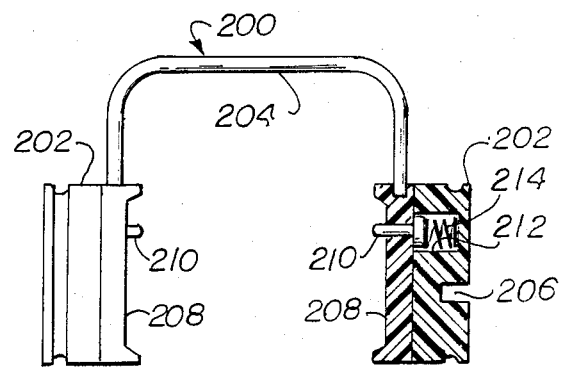
Figure 17:
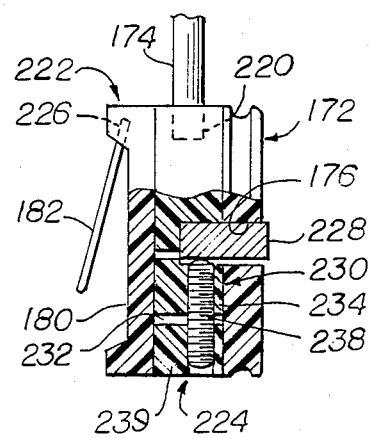

FIGS. 6A-6D, 7A-7D, and 8A-8D, respectively illustrate three additional embodiments of orthodonture appliance as designed in accordance with the present invention;

FIGS. 9A, 9B and 10-12 are diagrammatic illustrations of individual teeth having differently configured engagement protrusions bonded directly thereto;

FIG. 13 is a perspective view of part of an orthodonture appliance similar to the ones shown in FIGS. 4A and 4B but designed in accordance with another embodiment of the present invention;

FIG. 14 is a perspective view of part of an orthodonture appliance similar to the ones shown in FIGS. 4A and 4B but designed in accordance with still another embodiment of the present invention;

FIG. 15 is a perspective view of part of an orthodonture appliance similar to the ones shown in FIGS. 4A and 4B but designed in accordance with yet another embodiment of the present invention;

FIG. 16 is a front elevational view of an orthodonture appliance similar to the part illustrated in FIGS. 4A and 4B but designed in accordance with a further embodiment of the present invention; and FIG. 17 is a side elevational view of a part of an orthodonture appliance displaying still another feature of the appliance.

DESCRIPTION OF THE PREFERRED EMBODIMENTS

Figure 1:
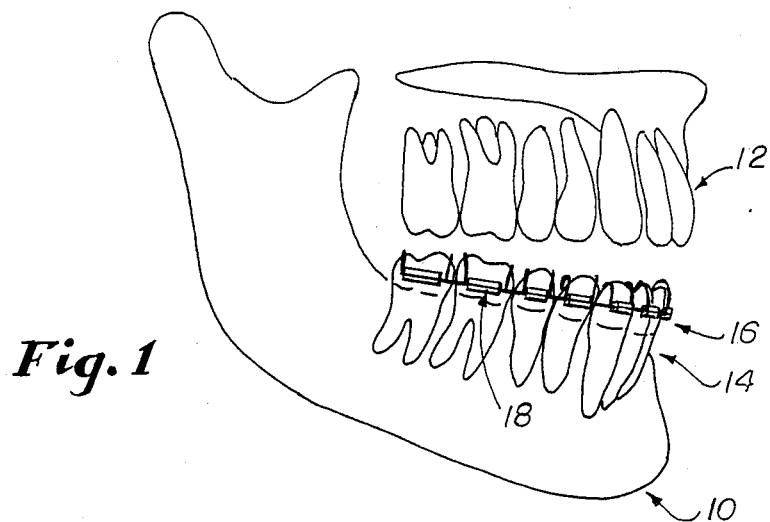
FIG. 1 is a side elevational view of a jaw in which an orthodonture appliance designed in accordance with a preferred embodiment of the present invention is installed.

Turning now to the drawings, wherein like components are designated by like reference numerals throughout the various figures, attention is first directed to FIGS. 1-4. FIG. 1 illustrates a patient's jaw 10 and particularly his upper and lower teeth 12 and 14, respectively. Lower teeth 14 are shown in combination with an orthodontic appliance 16 which is designed in accordance with the present invention. While the appliance is shown on the entire bottom row of teeth (see FIG. 2), it is to be understood that a similar appliance could be applied to the upper row of teeth and that the appliance can also be readily designed in accordance with the present invention for use with less than an entire row of teeth. However, for purposes of description, it will be assumed that only the patient's bottom row 14 is maloccluded and must therefore be moved to a more ideal position.

Figure 2:
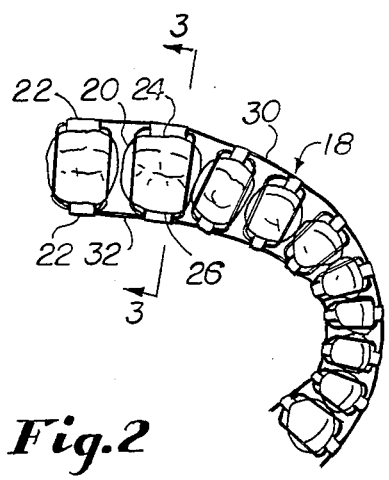
FIG. 2 is a plan view of the jaw of FIG. 1 taken generally along line 2—2 in FIG. 1.
Figure 3:
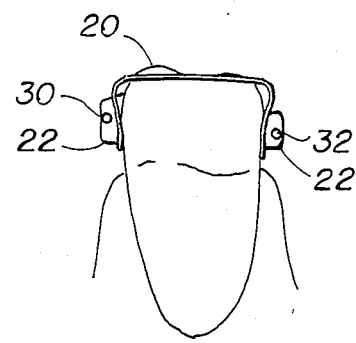
FIG. 3 is a cross-sectional view of one tooth of the jaw of FIG. 1, taken generally along line 3—3 in FIG. 2.

Referring specifically to FIGS. 2-4 in conjunction with FIG. 1, overall orthodontic appliance 16 is shown including a plurality of individual clasps 18 for gripping onto individual teeth such that they can be manually placed in gripping positions onto and manually disengaged from their respective teeth by the patient.

As best seen in FIG. 4A, each clasp includes two generally U-shaped spring tempered steel wire elements (or cross wires) 20 movable between a biased contracted state (narrower than or equal to the thickness of the tooth) and manually forced expanded state (wider than the thickness of the tooth from its facial side to its lingual side) whereby to clamp to an associated tooth. In this regard, the two clamping wires must be specifically sized and sufficiently spring tempered to adequately grip to its associated tooth while allowing the patient to be able to easily manually expand the U-shaped wires in order to place them on the tooth and remove them. As illustrated in FIG. 4A, opposite ends of each pair of wire elements forming a given clasp are connected together by cross brackets 22 which also form part of the clasp. This is accomplished by suitable bonding or soldering techniques or the like. Thus, when a given clasp is mounted over its cooperating tooth as, for example, in FIGS. 2 and 3, one of the cross brackets 22 engages the facial side 24 of its particular tooth (see FIG. 2) while the opposite confronting cross bracket engages the lingual side 26 of the same tooth, preferably at the natural undercuts of the tooth. At the same time, two wire elements 20 of each clasp cross over the mesial and distal marginal ridges of their associated tooth (again, see FIG. 2). In FIG. 4B the brackets 22 may be connected to a continuous wire 20'. In either case, if only one arch wire is used (to be described below) it may not be necessary to include both brackets.

In addition to the components thus far described, overall orthodonture appliance 16 includes a pair of continuous lengths of wire 30 and 32 arch wires which are connected at predetermined points along their lengths to each of the clasps in a particular way. Specifically when the clasps are in gripping positions on their respective teeth, as in FIG. 2, the arch wires 30 and 32 extend from tooth to tooth along the facial and lingual sides of the teeth, respectively and exert forces on the teeth to move them from malocclusion positions to the desired, more ideal positions. To this end, suitable and readily providable means are available for connecting the wires to the clasps. In the particular embodiment illustrated, the brackets 22 which are readily available in the art serve that purpose. By using two arch wires 30 and 32, the patient can readily remove the overall appliance without it falling apart or becoming bent as might occur if only one wire were used, although in special cases it may be desirable to use only one arch wire which may be located on the facial or lingual side of the teeth.

As will be seen hereinafter in conjunction with some of the later figures, brackets 22 themselves provide means for disengageably connecting arch wires 30 and 32 to the brackets so that they can be periodically adjusted by an orthodontist. As will also be seen hereinafter in conjunction with the later figures, the opposing brackets of each clasp preferably include confronting recesses configured to receive cooperating projections bonded on to the facial and lingual sides of an associated tooth whereby to aid the clasp in gripping its associated tooth. In this regard, as will also be seen, each bracket preferably includes its own through-hole so that the orthodontist may accurately provide marks on an associated tooth to locate cooperating artificial projections (e.g., buttons) on that particular tooth. Once located, the orthodontist or technician can readily provide the projections.

Having described orthodonture appliance 16 structurally, attention is now directed to the way in which the appliance is made for a particular patient. First, each clasp 18 is formed with a particular tooth in mind. It may be possible to provide standard clasp designs for certain teeth of certain patients. Before arch wires 30 and 32 are connected to these clasps, a mold of the patient's teeth in ideal positions may be made. This can be carried out in a known manner. Thereafter, the clasps are positioned over their corresponding teeth forming the ideal mold and the arch wires 30 and 32 are then connected to the clasps so as to establish a relatively tight fit. Thereafter, the appliance is ready to be fitted onto the patient's maloccluded teeth. As a result, the arch wires 30 and 32 will exert forces on the teeth to move the latter from the maloccluded positions to the ideal positions corresponding to the mold. However, appliance 16 can be fitted to the patient's teeth directly. Specifically, the orthodontist would fit the clasps to the patient's teeth and disengagably connect wires 30 and 32 in the desired way. In this way the wires can be configured to exert the appropriate forces on the teeth to move the latter to their desired position. Turning to FIGS. 5A-5D, a single tooth 34 is shown including an individual clasp 36 designed in accordance with a specific embodiment of the present invention. Clasp 36 includes spring tempered cross wire elements 20 which are connected together at opposite ends by particularly configured brackets 38 and 40. As best illustrated in FIGS. 5A and 5B, bracket 38 includes an inwardly facing recess 41 designed to receive a cooperating projection 42 on tooth 34. As best illustrated in FIGS. 5C and 5D, bracket 40 includes two such recesses 44 and 46 for receiving two cooperating projections 48 and 50, respectively, on the opposite side of the tooth as projection 42. Through-holes 52, 54 and 56 extending through bracket bodies 38 and 40 allow the orthodontist to mark the tooth prior to providing projections 42, 48 and 50 in order to accurately locate these projections.

Still referring to FIGS. 5A–5D, brackets 38 and 40 include outwardly opening cross slots 58 and 60, respectively, for receiving cooperating sections of the previously described wires 30 and 32 in order to disengageably connect the wires to the clasps. A set screw 62 (or other suitable means) extends through a cooperating opening in bracket 38 for engagement with the wire section in slot 58 in order to hold that section of the wire in place. Two such set screws 64 are provided in similar cooperating openings in bracket 40 for the same purpose.

It is to be understood that clasps corresponding to clasp 36 described immediately above could be utilized in place of clasps 18 in overall appliance 10 described in conjunction with FIGS. 1–4. Moreover, clasp 36 could be readily modified to include two brackets 38 rather than a bracket 38 and a bracket 40 or it could be readily modified to include two brackets 40. The spring tempered wires 20 could be readily connected to the brackets in any suitable manner, for example, by means of soldering or welding. Moreover, wire elements 20 and, in fact, wires 30 and 32 as well as brackets 38 and 40 can be constructed of any suitable material, for example stainless steel or nickel-titanium. However, these components could be constructed of other materials so long as they function in the manner described.

Referring now to FIGS. 6A–6D, a tooth 66 is shown in combination with still another type of clasp 68 which is also designed in accordance with the present invention. Clasp 68 includes a pair of spring tempered wires 20 connected at common ends to a bracket 38 corresponding to the one illustrated in FIG. 5. The other ends of these two wire elements are connected to a similar bracket 38 which also has connected thereto the common ends of two intermediate wire elements 70. The other ends of wire elements 70 are connected to a cap 72 which fits over a cooperating projection 74 from tooth 66. Thus, tooth 66 includes three projections, the projection 74 and projections cooperating with the two brackets 38. In this way, the overall clasp may better grip to tooth 66 than, for example, the clasp 36.

Turning now to FIGS. 7A–7D, still another tooth 74 is illustrated in combination with still another clasp 76 designed in accordance with the present invention. Clasp 76 does not use wire elements 20 as did the previously described clasps. Rather, clasp 76 utilizes a single generally U-shaped spring tempered metal band 78 which functions in the same manner as the two wire elements 20. That is, the band 78 is configured to be movable between a biased contracted state and a manually forced expanded state so as to grip around its associated tooth. In the particular embodiment shown, the band itself includes integrally formed recesses for receiving cooperating projections on tooth 74. One end of the band includes a single recess 80 for accommodating a single projection 82 and the opposite side of the band includes two recesses 84 for accommodating cooperating projections 86. Brackets 88 are fixedly mounted to opposite sides of the band 78, in the manner shown. These brackets include cross slots 58 corresponding to the cross slots illustrated in FIGS. 5A and 5B and cooperating set screws 62 or other suitable means for disengagably connecting wires 30 and 32 to the brackets.

While band 78 has been described as including a single recess on one side thereof and two recesses on the opposite side, it is to be understood that the band could be modified to include a single recess on each side or two recesses on each side. Moreover, while band 78 is preferably constructed of steel, it could be constructed of any other suitable material which functions in the manner intended.

Referring now to FIGS. 8A–8D, still another tooth 90 is shown in combination with still another clasp 92 designed in accordance with the present invention. Clasp 92, like the previously described clasp 76 includes a single spring tempered U-shaped band 94 which functions in the same manner as band 78, although it is slightly narrower across its entire extent. Band 94 includes a single inwardly facing recess 96 on each end for accommodating the cooperating projection 98 on tooth 90. Band 94 also includes a third inwardly facing recess 100 disposed within a section of the band which has been provided with relief 102 (see FIG. 8C). The recess 100 serves to accommodate a cooperating projection 104 on tooth 90. Suitable brackets 106 having wire receiving slots 108 and cooperating set screws (not shown) or other suitable means for holding the wire are fixedly connected to opposite sides of band 94. Again, it is contemplated that band 94 be constructed of metal, although like band 78 it may be constructed of other suitable material.

In any event, clasp 76 or any of the other clasps thus far described can be readily incorporated into appliance 16 described in conjunction with FIGS. 1–4 in place of the clasps 18 described there. Moreover, while all of these embodiments have described their respective projections as being generally circular in configuration, it is to be understood that the projections could be provided with other shapes depending upon the particular tooth. For example, the projections could be made elongated, either vertically or horizontally. In these cases, the cooperating recesses in the associated brackets would be provided with corresponding shapes. See for example FIGS. 7A–7D where the projection 82 is round and projections 86 are oblong.

FIGS. 5–8 illustrate individual teeth, individual clasps associated with the teeth and cooperating projections bonded directly to the teeth for aiding and securing the clasps thereto. For example, FIG. 5A–D illustrates projections 42, 48 and 50 bonded directly to tooth 34. Each bracket 38 includes a recess 41 designed to receive projection 42 and bracket 40 includes similar recesses for receiving projections 48 and 50. In all of the cases illustrated in FIGS. 5–8, the projections are shown somewhat semi-spherical in configuration. The present invention is not limited to this particular shape, as will be discussed in detail immediately below.

Referring to FIGS. 9A, 9B and FIGS. 10–12, various individual teeth are shown with different shaped projections. More specifically, FIGS. 9A and 9B illustrate tooth 120 supporting a projection 122 on one side thereof and a projection 124 on the opposite side. Like the previously described projections, these projections are bonded directly to the teeth by a suitable bonding substance, for example a dental composite adhesive. Note that the projection 122 has a beveled outer periphery 126 and a cross channel 128 which is provided for reasons to be described hereinafter. Projection 124 includes a similar cross channel 130 and may include a similar beveled outer periphery, although it is not shown. Moreover, the projection 124 is shown to be substantially shorter in length (the vertical dimension) than projection 122.

In FIG. 10, a tooth 132 is shown in combination with a projection 134 which not only includes a cross channel 136 but also a vertical slot 138 which is also provided for reasons to be discussed hereinafter. FIG. 11 illustrates a tooth 140 including a bonded projection 142 which is rectangular in configuration and which includes its own outer beveled periphery 144 and FIG. 12 illustrates a tooth 146 including a generally circular projection 148 including a beveled outer periphery 150 and both a cross channel 152 and a vertical slot 154.

Turning now to FIG. 13, attention is directed to a modified clasp 156 including opposing brackets 158 joined by a pair of cross wires 160. Each of the brackets includes outer cross slots 162 for containing cooperating sections of arch wires (not shown) and each bracket includes suitable means (not shown) for retaining these cooperating arch wire sections within slots 162. In addition, as illustrated in FIG. 13, each bracket 158 includes an inwardly facing recess 164 for receiving a cooperating projection. In the case of brackets 158, the recesses are configured to receive the rectangular projection similar to, for example, projection 134 shown in FIG. 10. Note specifically that a center bar 166 extends vertically downward across recess 164. This center bar is configured for insertion within, for example, vertical slot 138 in projection 134. In this case, the cross channel 136 is not used and, indeed, the projection could be provided without this cross channel when the projection is used with cooperating bracket 158. In any event, the center bar 166 aids in ensuring that the bracket reliably engages around and to its cooperating projection and, particularly, it minimizes the possibility of the bracket twisting.

FIG. 14 illustrates another clasp 170 including opposing brackets 172 and connecting cross wires 174. Like brackets 158 brackets 172 include similar cross slots 176 for accommodating arch wires and means generally indicated at 178 for fixing the arch wires with respect to the brackets. In addition, each bracket includes its own cooperating recess 180 for accommodating a cooperating projection bonded to an associated tooth. As illustrated in FIG. 14, a U-shaped spring element 182 is suitably mounted in each recess 180 and is shown by solid lines in the spring-loaded (biased) position. Note that the horizontal component of the U-shaped element is biased outwardly away from recess 180 but can be forced into the recess, as illustrated by dotted lines. When the clasp is mounted over a cooperating tooth in the typical manner described previously, each recess 180 fits over a cooperating projection corresponding in configuration. The horizontal part of each U-shaped wire element 182 is positioned to fit within a cooperating cross slot in the projection and, because of its bias, it engages positively within the slot. This ensures that the bracket reliably engages its associated projection.

FIG. 15 illustrates a single bracket 190 which forms part of an overall clasp similar to the ones described previously. To this end, bracket 190 includes a corresponding cross slot 192 for receiving a section of an arch wire and means (not shown) for locking the cross wire within the slot. In addition, the bracket includes its own recess 194 for accommodating a similarly shaped projection bonded to a tooth. Moreover, as illustrated in FIG. 15, a band-shaped spring member 196 extends horizontally across recess 194 and is connected to the bracket in a spring-loaded fashion, similar to U-shaped element 182 and for a similar purpose, that is to engage within a cooperating cross slot in the associated projection.

Turning now to FIG. 16, still another clasp 200 is shown there. This clasp includes brackets 202 connected together by cross wires 204 and each bracket includes cross slots 206 for cooperating arch wires.

Again, while not shown, brackets 202 include means for holding the arch wires within the slots 206. Moreover, each of the brackets includes a cooperating recess 208 for accommodating an associated projection. Each bracket 202 includes a spring-loaded plunger 210 having a free end which extends into a cooperating recess 208. The back end of the plunger is mounted within a cooperating opening 212 which contains a coil spring 214 for biasing the plunger inwardly into its associated recess. In that way, when the clasp is fitted over a cooperating tooth and each recess is positioned around a cooperating projection, each plunger is biased into a cooperating opening in the plunger. Clasp 200 may be used, for example, in conjunction with tooth 120 such that the plungers 210 extend into cross grooves 128 and 130 or a cooperating circular opening (not shown) in place of the cross grooves.

Referring now to FIG. 17, one of the previously described brackets 172 (see FIG. 14) is illustrated in side elevational view connected to one end of a cross wire 174. The cross wire is soldered, welded or otherwise suitably mounted within a cooperating opening 220 in the bracket. In this regard, for ease of manufacture, the bracket itself may be constructed of two separate parts 222 and 224 and subsequently bonded together by suitable means. Part 222 defines previously described recess 180 and spring clip 182 which may be soldered, welded or otherwise bonded into cooperating slots in part 222, as generally indicated at 226. Part 224 is shown including cross slot 176 for accommodating a section of an arch wire which is generally indicated at 228. The arch wire is held in place by means of a lug arrangement 230 disposed within a cooperating opening 232 in part 224. Lug arrangement 230 includes a lug 234 having an internal threaded opening for receiving captured bolt 238 mounted within opening 232 and through cross support 239 for rotation only. By rotating bolt 238, the lug 234 is able to move up and down along its length so as to tightly engage the arch wire and hold it in place within cross slot 176. Because overall bracket 172 is constructed of two parts, it is relatively simple to provide opening 232.

It is to be understood that all of the brackets described above, where applicable, could be constructed in two or more pieces in order to facilitate manufacturing of these components. Moreover, it is to be understood that the various features making up the various clasp configurations, as described above, could be interchanged, again where appropriate. Further the appliance disclosed herein could be used to provide movement between the upper and lower jaws of a patient. In that case, the patient would wear one on his upper teeth and one on his lower teeth with the two appliances being interconnected in the desired way. It is also to be understood that any of the appliances described could be provided with second slots on the facial or lingual brackets to accommodate second arch wires o either side of the appliance.

It is to be further understood that suitable means other than those described above could be utilized to disengageably connect the arch wires with the brackets. Such means could, for example, include the well known Begg style pin and tube approach.

What is claimed is:

1. An appliance for orthodonture characterized in that at least most of said appliance may be installed and removed by the patient as required, said appliance comprising:
(a) a plurality of individual clasps for respectively gripping onto individual upper or lower teeth of the patient, each of said clasps being configured such that they can be individually manually placed in gripping positions onto and manually disengaged from said teeth by the patient wherein, each of said clasps including at least one generally U-shaped spring tempered element movable between a biased contracted state and a manually forced expanded state whereby to clamp to an associated tooth;
(b) first and second continuous lengths of wire; and
(c) means for disengageably connecting each of said wires at predetermined points along its length to each of said clasps such that when the clasps are in gripping positions on their respective teeth, said wires extend from tooth to tooth along the facial and/or lingual sides of the teeth, respectively, and exert forces on the teeth to move the latter from malocclusion positions to desired, more ideal positions.

2. An appliance according to claim 1 wherein said wire connecting means includes a bracket connected to each end of each of said generally U-shaped clamping elements such that when the clamping elements are in clamped positions on their respective teeth a first group of said brackets are engaged against the facial sides of the teeth while a second group of said brackets engage against the lingual sides of the teeth, and wherein each of said brackets includes means for disengagably connecting it to one of said continuous wires at a particular point along the length of the wire.

3. An appliance according to claim 2 wherein each of said generally U-shaped clamping element is a spring tempered cross wire and wherein each clasp includes two such cross wires which extend over the occlusal surfaces of an associated tooth when the clasps are in their gripping positions.

4. An appliance according to claim 3 wherein said cross wires extend over the mesial and distal marginal ridges of said occlusal surfaces.

5. An appliance according to claim 3 wherein the brackets connected to opposite ends of each clamping element include confronting recesses configured to receive cooperating projections bonded onto the facial and lingual sides of an associated tooth whereby to aid the clamping element in gripping that tooth.

6. An appliance according to claim 5 wherein said confronting recesses are of different shapes for receiving different shaped projections.

7. An appliance according to claim 5 wherein the brackets connected to opposite ends of each clamping element include a plurality of said confronting recesses configured to receive an equal plurality of cooperating projections bonded onto the facial and lingual sides of an associated tooth.

8. An appliance according to claim 5 wherein one of said last-mentioned brackets includes one of said recesses while the other of said last-mentioned brackets includes more than one such recess.

9. An appliance according to claim 2 wherein said generally U-shaped element includes integrally formed therein a pair of confronting recesses configured to receive cooperating projections bonded onto the facial and lingual sides of an associated tooth whereby to aid the clamping element in gripping the tooth.

10. An appliance according to claim 1 wherein each of said clasps includes a pair of generally U-shaped spring tempered wire elements movable between biased contracted states and manually forced expanded states whereby to clamp to an associated tooth such that the two wire elements extend over the occlusal surfaces of that tooth.

11. An appliance according to claim 10 wherein said cross wires extend over the mesial and distal marginal ridges of said occlusal surfaces.

12. An appliance according to claim 10 wherein each of said clasps includes only said pair of generally U-shaped spring tempered wire elements and no more than said two elements.

13. An appliance according to claim 1 wherein each of said clasps includes only one generally U-shaped spring tempered element, the latter being in the form of a band.

14. An appliance according to claim 1 wherein each of said clasps includes at least three generally U-shaped spring tempered wire element movable between biased and contracted states and manually forced expanded states, whereby to clamp to an associated tooth.

15. An appliance according to claim 14 wherein each of said clasps includes four of said wire elements.

16. An appliance for orthodonture characterized in that at least most of said appliance may be installed and removed by the patient as required, said appliance comprising:
(a) a plurality of individual clasps for respectively gripping onto upper or lower teeth of the patient, each of said clasps being configured such that they can be manually placed in gripping positions onto and manually disengaged from said teeth by the patient, each of said clasps including at least one generally U-shaped spring tempered element movable between a biased contracted state and a manually forced expanded state whereby to clamp to an associated tooth;
(b) a single continuous arch wire; and
(c) means for disengageably connecting said arch wire at predetermined points along its length to each of said clasps such that when the clasps are in gripping positions on their respective teeth, said wire extends from tooth to tooth along either the facial or lingual side of the teeth, and exerts forces on the teeth to move the latter from malocclusion positions to desired, more ideal positions.

17. A clasp for use as part of an orthodonture appliance which is readily installed and removable by the patient, said clasp comprising:
(a) at least one generally U-shaped spring tempered element movable between a biased contracted state and a manually forced expanded state, whereby to be manually placed in a gripping position onto and manually disengaged from an associated tooth by the patient; and
(b) means for disengagably connecting said U-shaped element to at least one arch wire also forming part of said appliance such that the arch wire exerts the desired forces on the patient's teeth when the overall appliance is worn by the patient.

18. A clasp according to claim 17 wherein said wire connecting means includes a bracket connected to each end of each generally U-shaped clamping element such that when the clamping element is in a clamped position on its associated tooth one bracket is engaged against the facial side of the tooth while a second bracket engages against the lingual side of the tooth, and wherein at least one of said brackets includes means for disengageably connecting it to said one wire at a particular point along the length of the wire.

19. A clasp according to claim 18 wherein said generally U-shaped clamping element is a spring tempered wire and wherein said clasp includes two such wires which extend over the occlusal surfaces of an associated tooth when the clasp is in its gripping position.

20. A clasp according to claim 18 wherein the brackets connected to opposite ends of each clamping element include confronting recesses configured to receive cooperating projections bonded onto the facial and lingual sides of an associated tooth whereby to aid the clamping element in gripping that tooth.

21. A clasp according to claim 20 wherein said confronting recesses are of different shapes for receiving different shaped projections.

22. A clasp according to claim 20 wherein the brackets connected to opposite ends of each clamping element including a plurality of said confronting recesses configured to receive an equal plurality of cooperating projections bonded onto the facial and lingual sides of an associated tooth.

23. A clasp according to claim 20 wherein one of said last-mentioned brackets includes one of said recesses while the other of said last-mentioned brackets includes more than one such recess.

24. A clasp according to claim 18 wherein said generally U-shaped element includes integrally formed therein a pair of confronting recesses configured to receive cooperating projections bonded onto the facial and lingual sides of an associated tooth whereby to aid the clamping element in gripping the tooth.

25. A clasp according to claim 17 including a pair of generally U-shaped spring tempered wire elements movable between biased contracted states and manually forced expanded states whereby to clamp to an associated tooth such that the two wire elements extend over the occlusal surfaces of that tooth.

26. A clasp according to claim 25 including only said pair of generally U-shaped spring tempered wire elements and no more than said two elements.

27. A clasp according to claim 17 including only one generally U-shaped spring tempered element, the latter being in the form of a band.

28. A clasp according to claim 17 including at least three generally U-shaped spring tempered wire element movable between biased and contracted states and manually forced expanded states, whereby to clamp to an associated tooth.

29. A method of providing an orthodonture appliance which may be installed and removed by the patient as required, said method comprising the steps of:
(a) providing a plurality of individual clasps for gripping onto individual upper or lower teeth of the patient, said clasps being configured such that they can be manually placed in gripping positions onto and manually disengaged from said teeth by the patient;
(b) providing a first continuous length of wire;
(c) disengageably connecting said wire at predetermined points along its length to each of said clasps such that when the clasps are in gripping positions on their respective teeth, said wire extends from tooth to tooth along one of the facial and lingual sides of the teeth and exerts forces on the teeth to move the latter from malocclusion positions to desired, more ideal positions; and (d) said individual clasps including recesses configured to receive cooperating projections bonded on the facial and lingual sides of an associated tooth whereby to aid the clasps in gripping their respective teeth, said method including the steps of providing said projections on the facial and lingual sides of each applicable tooth.

30. A method according to claim 29 including the step of disengageably connecting a second continuous length of wire to each of said clasps in the same manner as said first wire but on the opposite side of the tooth.

31. A method according to claim 30 including the step of initially placing said clasps in their gripping positions on the respective teeth of said patient before connecting said first and second wires thereto and thereafter connecting said wires to said clasps while the latter are in their gripping positions in order to establish the desired forces to be applied to the teeth.

32. An orthodonture arrangement for use on certain teeth of a patient, comprising:
(a) a pair of projections adapted to be bonded directly to the facial and lingual sides of each of said teeth; and
(b) an orthodonture appliance including means for gripping directly each of said teeth around its respective projections and means connected to said gripping means for exerting forces on said teeth to move the latter from malocclusion positions to desired, more ideal positions, said gripping means being configured so that the patient can readily remove the orthodonture appliance at will, leaving only said projections.

33. An arrangement according to claim 32 wherein said gripping means includes a plurality of individual clasps for gripping directly onto individual ones of said teeth, each of said clasps being configured such that they can be manually placed in gripping positions onto and manually disengaged from said teeth by the patient.

34. An arrangement according to claim 33 wherein said clasps include recesses corresponding in configuration to and fitting over cooperating ones of said projections when the clasps are in said gripping positions.

35. An arrangement according to claim 34 wherein at least some of said projections include their own recesses and wherein cooperating brackets include means extending into said recesses.

36. An arrangement according to claim 35 wherein said last-mentioned means includes spring-loaded elements biased in positions engaging the recesses of their associated projections.

37. An arrangement according to claim 36 wherein each of said brackets including said last-mentioned means includes at least two integrally formed components bonded together.

38. An arrangement according to claim 32 wherein each of said clasps includes at least one generally U-shaped spring tempered element movable between a biased contracted state and a manually forced expanded state whereby to clamp to an associated tooth.

39. A method of providing an orthodonture appliance which may be installed and removed by the patient as required, said method comprising the steps of:
(a) providing a plurality of individual clasps for gripping onto individual upper or lower teeth of the patient, said clasps being configured such that they can be manually placed in gripping positions onto and manually disengaged from said teeth by the patient;

(b) providing a first continuous length of wire;

(c) disengageably connecting said wire at predetermined points along its length to each of said clasps such that when the clasps are in gripping positions on their respective teeth, said wire extends from tooth to tooth along one of the facial and lingual sides of the teeth and exerts forces on the teeth to move the latter from malocclusion positions to desired, more ideal positions; and (d) each of said individual clasps including a recess configured to receive a cooperating projection bonded on the facial or lingual sides of an associates tooth whereby to aid the clasps in gripping their respective teeth, said method including the step of providing said projections.

40. A method according to claim 39 wherein said projection is bonded on the facial sides of each associated tooth.

41. A method according to claim 39 wherein said projection is bonded on the lingual side of each associated tooth.

42. An orthodonture arrangement for use on certain teeth of a patient, comprising:

(a) a projection adapted to be bonded directly to the facial or lingual side of each tooth;

(b) an orthodonture appliance including means for gripping directly each of said teeth around its respective projection and means connected to said gripping means for exerting forces on said teeth to move the latter from malocclusion positions to desired, more ideal positions, said gripping means being configured so that the patient can readily remove the orthodonture appliance at will, leaving only said projections.

43. An arrangement according to claim 42 wherein said projection is bonded on the facial side of each associated tooth.

44. An arrangement according to claim 42 wherein said projection is bonded on the lingual side of each associated tooth.

* * * * *